US00PP14798P3

(12) United States Plant Patent
Olesen et al.

(10) Patent No.: US PP14,798 P3
(45) Date of Patent: May 18, 2004

(54) MINIATURE ROSE VARIETY 'POULHI005'

(50) Latin Name: *Rosa hybrida*
Varietal Denomination: POULhi005

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/177,230

(22) Filed: Jun. 21, 2002

(65) Prior Publication Data

US 2003/0237119 P1 Dec. 25, 2003

(51) Int. Cl.[7] ..... A01H 5/00

(52) U.S. Cl. ..... Plt./122

(58) Field of Search ..... Plt./122

*Primary Examiner*—Bruce R. Campell
*Assistant Examiner*—Annette H Para

(57) ABSTRACT

A new miniature rose which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

Botanical classification: *Rosa hybrida.*

Variety denomination: 'POULhi005'.

Commercial classification: Miniature Rose Plant.

The present invention constitutes a new and distinct variety of miniature rose plant which originated from a controlled crossing between 'POULsabel', described and illustrated in U.S. Plant patent application Ser. No. 09/607, 333 dated Jun. 30, 2000 and an unnamed, not patented seedling. The two parents were crossed and the resulting seeds were planted in a controlled environment. The new variety is named 'POULhi005'.

The new rose may be distinguished from its seed parent, 'POULsabel', by the following combination of characteristics:

1. The general tonality of 'POULsabel' is Red Group 53A, while that of 'POULhi005' is Red Group 45B.
2. The blooms of 'POULsabel' are borne singly, while those of 'POULhi005' are borne 5 to 7 per flowering stem.
3. The shape of 'POULsabel''s petals is deltoid, while those of 'POULhi005' are obovate.

The new variety may be distinguished from its pollen parent, an unnamed seedling, created by the same inventors, by the following combination of characteristic:

1. The general tonality of the unnamed pollen parent is darker than that of 'POULhi005'.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULhi005' from all other varieties of which we are aware. As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhi005' was selected by the inventors as a single plant from the progeny of the hybridization in May of 1999. Asexual reproduction of 'POULhi005' by cuttings and traditional budding was first done by L. Pernille and Mogens N. Olesen in their nursery in Fredensborg, Denmark in October 1999. This initial and other subsequent propagations conducted in controlled environments have demonstrated that the characteristics of 'POULhi005' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULhi005'. Specifically illustrated in SHEET 1:

1. Stems showing branching and the attachment of leaves, buds, and peduncles;
2. Flower buds,
3. Flower petals,
5. Stems, exhibiting thorns;
6. Leaves.

DETAILED DESCRIPTION OF THE VARIETY

The following is a description of 'POULhi005', as observed in its growth in a field nursery in Jackson County, Oreg. The observed plants are 3 years of age. Color references are made using The Royal Horticultural Society (London, England) Colour Chart, 1995, except where common terms of color are used.

For a comparison, several physical characteristics of the rose variety 'POULhappy', a rose variety from the same inventors described and illustrated in U.S. Plant Pat. No. 9,483 and issued on Mar. 26, 1996 are compared to 'POULhi005' in Chart 1.

CHART 1

| | 'POULhi005' | 'POULhappy' |
|---|---|---|
| Petalage | 32 to 34 | 25 to 30 |
| Petal color, upper surface | Red Group 44B | Red Group 46B |
| Petal color, lower surface | Red Group 45B | Red Group 46B |

Parents: 'POULsabel' × an unamed seedling.

FLOWER AND FLOWER BUD

Blooming habit: Continuous.

Flower bud:

*Size.*—Upon opening, 28 mm in length from base of receptacle to end of bud.

*Bud form.*—Long; pointed ovoid.

*Bud color.*—As sepals unfold, upper surface of sepals is Red Group 45B; lower surface is Red Group 45A.

*Sepals.*—Green Group 144B in marginal zones; middle zone is Greyed-Orange Group 176A with intonations of Red-Purple Group 59c. Weak foliaceous appendages on three of the five sepals. Surfaces of sepals moderately pubescent. Stipitate glands are present in very small quantities. Shape: Sepal apex is cirrose. Base is flat at union with peduncle. Size: 25 mm long×8 mm wide.

*Receptacle.*—Surface: Smooth. Shape: Funnel-shaped. Size: 5 mm (h)×6 mm (w). Color: Yellow-Green Group 144A.

*Peduncle.*—Surface: Moderate quantities of stipitate glands. Length: 20 to 30 mm average length. Color: Yellow-Green Group 144A, with occasional intonations of Red-Purple Group 60C. Strength: Strong.

*Borne.*—5 to 7 buds per stem.

Flower bloom:

*Fragrance.*—None.

*Duration.*—As a pot plant, flowers last from 6 to 8 days. Petals fall cleanly away from plant.

*Size.*—Medium for a 12–15 cm pot rose. Average flower diameter is 50 mm when open.

*Form.*—Shape of flower when viewed from the side: Upon opening, upper part: Convex. Upon opening, lower part: Flat. Open flower, upper part: Convex. Open flower, lower part: Concave.

*Petalage.*—Average range: 32 to 35 petals under normal conditions with 3 to 5 petaloids.

Color:

*Upon opening, petals.*—Outermost petals: Outer Side: Red Group 45B. Inner Side: Red Group 44B, with occasional vertical white streak of White Group 155A. Innermost petals: Outer Side: Red Group 45B. Inner Side: Red Group 44B, with occasional vertical white streak of White Group 155A.

*Upon opening, basal petal spots.*—Outermost petals: Outer Side: White Group 155A. Inner Side: White Group 155A. Innermost petals: Outer Side: White Group 155A. Inner Side: White Group 155A.

*After opening, petals.*—Outermost petals: Outer Side: Red Group 45B. Inner Side: Red Group 44B. Innermost petals: Outer Side: Red Group 45B. Inner Side: Red Group 44B.

*After opening, basal petal spots.*—No distinctive coloration at petal base observed. Outermost petals: Outer Side: White Group 155A. Inner Side: White Group 155A. Innermost petals: Outer Side: White Group 155A. Inner Side: White Group 155A.

General tonality: On open flower Red Group 45B. No change in the general tonality at the end of the $6^{th}$ day. Afterwards, general tonality is Red Group 50A.

Petals:

*Petal reflex.*—Slight.

*Petal edge.*—Entire. Some petals have point in center of margin.

*Shape.*—Rounded obovate.

*Petaloids.*—Quantity: 3 to 5. Size: 14 mm long; 11 mm wide. Color: Red Group 45B.

*Thickness.*—Average.

*Arrangement.*—Formal.

*Persistence.*—Flowers are self cleaning.

*Duration.*—Flowers persist on plant 10 to 12 days.

Reproductive organs:

*Pistils.*—Length: 5 to 8 mm long. Quantity: 45 to 50.

*Pollen.*—None observed.

*Anthers.*—Size: 2 mm long. Color: Greyed-Green Group 196D. Quantity: 35–40.

*Filaments.*—Color: Yellow-Green Group 150D. Length: 4 to 6 mm.

*Stigmas.*—Superior in location to anthers. Color: Greyed-Yellow Group 160C.

*Styles.*—Color: Greyed-Yellow Group 160C. Rose Hips: Color: Yellow Green Group 144A. Size: 10 mm.

PLANT

Plant growth: Vigorous, compact, upright to bushy. When grown as a 12–15 cm pot plant, the average height of the plant is 20 cm and the average width is 20 to 25 cm.

Stems:

*Color.*—Young wood: Yellow-Green Group 144A. Older wood: Yellow-Green Group 144A.

*Thornes.*—Incidence: 0 to 1 per 10 cm of stem. Size: Average length: 5 to 7 mm. Color: Greyed-Yellow Group 160C. Shape: Linear.

*Surface.*—Young wood: Smooth. Older wood: Smooth.

Plant foliage: Normal number of leaflets on leaves in middle of the stem: 5 leaflets.

*Leaf size.*—120 mm (l)×85 mm (w).

*Quantity.*—Abundant.

*Color.*—Upper Leaf Surface: Green Group 137A. Lower Leaf Surface: Green Group 137D. Juvenile foliage: Upper Leaf Surface: Green Group 137B. Lower Leaf Surface: Green Group 137D. Anthocyanin intonation: Location: On plants grown under high light conditions, leaf margins, developing leaves, peduncles, and stems may exhibit intonations of Greyed-Red Group 185A.

Plant leaves and leaflets:

*Stipules.*—Size: 18 to 20 mm. Color: Green Group 137D.

Presence of stipitate glands: On edges of stipules.

*Petiole.*—Size: 10 mm from base to first leaflet and 1 to 2 mm wide. Texture: Smooth. Color: Yellow Green Group 144A; interior is Greyed-Red Group 181C. Underneath: Yellow-Green Group 144A. Margins:

Yellow-Green Group 144A. Anthocyanin: When present, Greyed-Red Group 181C.

*Rachis.*—Color: Yellow Green Group 144A; interior is Greyed-Red Group 181C. Underneath: Yellow-Green Group 144A. Margins: Yellow-Green Group 144A. Anthocyanin: When present, Greyed-Red Group 181C.

*Leaflet.*—Edge: Serrated. Shape: Ovate. Glossiness: Moderately glossy. Arrangement: Odd pinnate. Venation: Reticulate.

Disease resistance: Average resistance to mildew, black spot, and Botrytis under normal growing conditions in Jackson County, Oreg.

Cold hardiness: 'POULhi005' has been found to be resistant to damage from cold, heat and drought damage in USDA Zone 7.

We claim:

1. A new and distinct variety of rose of the miniature class, substantially as herein illustrated and described as a distinct and novel rose variety due to its abundant, red flowers, vigorous growth, compact habit, suitability for production from softwood cuttings in pots, and durable flowers and foliage which make the variety suitable for distribution in the floral industry.

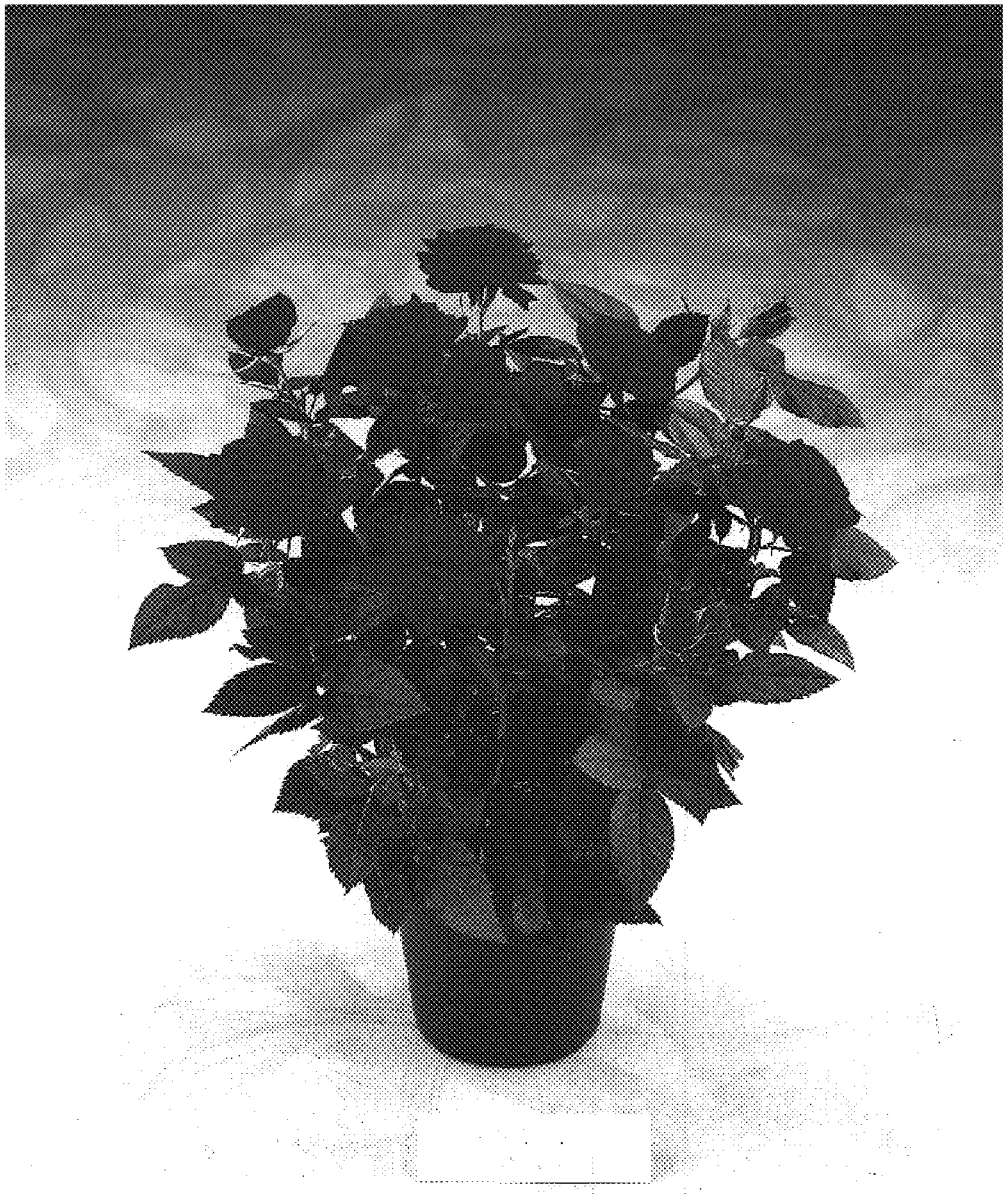

* * * * *